United States Patent [19]

McDaniel, Jr. et al.

[11] Patent Number: 4,557,729
[45] Date of Patent: Dec. 10, 1985

[54] COLOR STABILIZATION OF GLYCOSIDES

[75] Inventors: Robert S. McDaniel, Jr.; Paul R. Glor, both of Decatur; Hunter L. Kickle, Mt. Zion, all of Ill.

[73] Assignee: A. E. Staley Manufacturing Company, Decatur, Ill.

[21] Appl. No.: 613,923

[22] Filed: May 24, 1984

[51] Int. Cl.$^4$ .................................................. D06L 3/02
[52] U.S. Cl. .......................................... 8/111; 8/110; 252/174.17
[58] Field of Search ................. 8/110, 111; 252/174.17

[56] References Cited

U.S. PATENT DOCUMENTS

| | | | |
|---|---|---|---|
| 2,072,665 | 3/1937 | Campbell et al. | 8/110 |
| 2,172,233 | 9/1939 | Wilson | 8/110 |
| 2,860,945 | 11/1958 | Dustman, Jr. | 8/111 |
| 2,875,018 | 2/1959 | Easton et al. | 8/111 |
| 3,077,372 | 2/1963 | Smolens et al. | 8/111 |
| 3,086,534 | 4/1963 | Gorter et al. | 8/111 |
| 3,114,192 | 12/1963 | Matray et al. | 8/111 |
| 3,219,656 | 11/1965 | Boettner | 536/18.3 |
| 3,345,303 | 10/1967 | Schmid et al. | 8/111 |
| 3,378,444 | 4/1968 | Swanson | 8/110 |
| 3,450,690 | 6/1969 | Gibbons et al. | 536/18.5 |
| 3,547,828 | 12/1970 | Mansfield et al. | 252/351 |
| 3,640,998 | 2/1972 | Mansfield et al. | 536/18.3 |
| 3,960,649 | 6/1976 | Sullivan | 8/110 |
| 3,962,030 | 6/1976 | Sullivan | 8/110 |
| 3,974,138 | 8/1976 | Lew | 536/18.6 |
| 3,997,659 | 12/1976 | Knohl et al. | 8/111 |
| 4,154,706 | 5/1979 | Kankare et al. | 252/174.21 |
| 4,393,203 | 7/1983 | Mao et al. | 536/124 |

FOREIGN PATENT DOCUMENTS

| | | |
|---|---|---|
| 77167 | 4/1983 | European Pat. Off. |
| 96917 | 12/1983 | European Pat. Off. |
| 99183 | 1/1984 | European Pat. Off. |
| 102558 | 3/1984 | European Pat. Off. |

OTHER PUBLICATIONS

U.S. Ser. No. 573,905 filed Jan. 25, 1984, McDaniel.
U.S. Ser. No. 538,700 filed Oct. 3, 1983, VanderBurgh.

*Primary Examiner*—Paul Lieberman
*Assistant Examiner*—Willie J. Thompson
*Attorney, Agent, or Firm*—James B. Guffey; Michael F. Campbell; Philip L. Bateman

[57] ABSTRACT

Desirable color of glycosides are obtained through bleaching and stabilization with a source of sulfur dioxide.

12 Claims, No Drawings

COLOR STABILIZATION OF GLYCOSIDES

BACKGROUND OF THE INVENTION

1. Field of the Invention

This invention relates to glycoside materials.

2. Description of the Art Practices

It has long been known that alkyl glycosides have surfactant properties and are therefore desirable as either the sole surfactant, or in combination with other surfactants, in cleaning products. A glycoside as used herein means a material which contains 1 or more units of a sugar source such as glucose and a hydrophobic organic tail. If the glycoside contains glucose units, then it is referred to as a glucoside. If the glycoside contains 2 units of glucose, e.g. a polymer, then the material is referred to as a glycoside having a degree of polymerization (D.P.) of 2. If the glycoside is an alkyl glycoside then the material is substituted in the one position with an alkoxyl moiety rather than the $C_1$ hydroxyl of the starting sugar. Therefore, the attachment of the alkoxyl moiety is by an acetal linkage to the sugar.

It has been suggested by Boettner in U.S. Pat. No. 3,219,656 issued Nov. 23, 1965 that an acid catalyzed route for obtaining an alkyl polyglycoside (APG) may be utilized starting with a saturated alcohol and dextrose. Similarly, Mansfield in U.S. Pat. No. 3,547,828 issued Dec. 15, 1970 teaches a method of obtaining glycosides.

U.S. Pat. No. 3,974,138 issued to Lew on Aug. 10, 1976 states that it is preferable to use glucose as a starting material for the preparation of butyl polyglycoside. It has been observed, according to Lew, that it is extremely difficult when starting with the sugar source to obtain higher alkyl polyglycosides directly. That is, the starting sugar materials are highly water-soluble whereas dodecyl alcohol (to add a $C_{12}$ group) is extremely water-insoluble. Therefore, the route proposed by Lew is to form an intermediate butyl glycoside and to thereafter transetherify to obtain the higher alkyl polyglycosides. In such a reaction, butyl alcohol is generated as a by-product.

The removal of alcohols formed in transetherification is described by Mao in U.S. Pat. No. 4,393,203 issued July 12, 1983. In the disclosure, Mao states that it is desirable to remove the alcohol formed because of its adverse effect on the surfactant properties of the alkyl polyglycoside. Mao further states that the color properties of his product are not adversely affected by the processing described in his patent.

European Patent Application No. 82305283.5, published as 0077167 on Apr. 20, 1983 states that various reducing agents may be utilized in the processing of alkyl polyglycosides. The teachings of the 0077167 publication are that the reducing agent must be present with an acid catalyst which is used to react the alcohol with an aldose or ketose. The reducing agents stated to be useful are acids such as phosphorous, hypophosphorous, sulfurous, hyposulfurous, nitrous and hyponitrous acids. It is further stated that the composition containin the reducing agent remains in the acid form.

European Patent Application No. 83200771.0 published on Dec. 28, 1983 as 0096917 to Farris describes the preparation of alkyl glycosides using an acid catalyst at from 80° C. to 150° C. The 0096917 publication further states that a long-chain monohydric alcohol is used to form the glycoside by continuously or incrementally adding the monosaccharide and catalyst such that no more than 10% by weight of unreacted monosaccharide is present at any given time and that the average amount of unreacted monosaccharide not exceed 5% by weight of the mix. The stated reason for controlling the amount of saccharide present in the reaction mix of Farris is so that there is substantially a single phase present. U.S. Pat. No. 3,450,690 to Gibbons issued June 17, 1969 discusses the use of alkaline materials to remove alkali sensitive color bodies from an alkyl glucoside mixture.

European published application No. 102,558 discloses borates as being useful in preparing glycosides. It is further known that N-methyl-2-pyrrolidone may be utilized as a reaction medium to obtain a substantially single phase reaction between a saccharide and an alcohol to form an alkyl glycoside. It is also known that long-chain alkyl glycosides may be formed directly from a saccharide by utilizing a small amount of a previously prepared long-chain alkyl glycoside to render the saccharide and the alcohol compatible.

It has been disclosed in European published application No. 0099183 of Short (Jan. 25, 1984) that saccharides may be converted into glycosides of up to 6 carbon atoms by forming a liquid dispersant system containing the monohydric alcohol to be added. The liquid dispersant system includes acetone, ethylene glycol, methanol or ethanol and about 2 to 25 moles of water per saccharide molar unit. This reaction is stated to take place at superatmospheric pressure to maintain the dispersants in a liquid state.

The art has recognized several methods of obtaining and treating glycosides, yet color of the end product remains a problem. There has as yet not been an effective manner of maintaining a glycoside in a desirable lightly colored state. That is, alkyl glycosides as obtained are a dark amber color and for many uses, such as cosmetics or detergent products, it is desirable that they have no more than a straw yellow color.

It has been observed herein that even in products which have been decolorized that the color will degrade in the product upon standing. Therefore, it is desirable, and the present invention deals with, obtaining and stabilizing good color in alkyl glycosides.

Throughout the specification and claims, percentages and ratios are by weight, temperatures are degrees Celsius and pressures are in atmospheres over ambient unless otherwise indicated.

To the extent that such references are applicable, each of the foregoing is incorporated herein by reference.

SUMMARY OF THE INVENTION

This invention describes a process for bleaching organic materials including glycoside surfactants comprising the steps of:

(a) obtaining a mixture of the organic material;

(b) exposing the organic material to hydrogen peroxide; and (c) exposing the mixture of the organic material and the hydrogen peroxide to a source of sulfur dioxide; and recovering the bleached organic material from the process.

A further aspect of the invention is a process for bleaching an organic material including glycosides comprising the steps of:

(a) obtaining an aqueous solution of the organic material;
(b) exposing the organic material to a first bleaching agent; and
(c) then exposing the mixture of the organic material and the first bleaching agent to a source of sulfur dioxide in salt form; and recovering the bleached organic material from the process.

A third embodiment is a process for stabilizing the color of an organic material including glycosides comprising the steps of:
(a) obtaining an aqueous solution of a glycoside;
(b) thereafter introducing a sufficient amount of a source of sulfur dioxide to stabilize the color of the glycoside, thereby substantially avoiding color degradation of the glycoside.

The product described herein is a composition of matter comprising a bleached glycoside and a sufficient amount of a source of sulfur dioxide to substantially inhibit color degradation of the glycoside.

DETAILED DESCRIPTION OF THE INVENTION

The present invention allows for the conventional preparation of alkyl glycosides such as described in any of the references incorporated herein. Basically, a long-chain alcohol preferably containing from 6 to 22, preferably 8 to 20, carbon atoms and which is saturated is reacted onto the saccharide molecule. The addition of the long-chain alcohol may be by way of an intermediate such as by first obtaining a methyl through hexyl glycoside and then by transalcoholysis to obtain the long-chain alkyl glycoside. The direct route of going from the sugar to the long-chain glycoside may also be utilized.

The term polyglycoside refers to a D.P. 2 and higher material. It is also to be noted herein that the D.P. value is stated as an average insofar as a mixture of glycosides will be obtained. That is, when starting with polysaccharides, it would be expected that D.P. 1 through higher materials, e.g. D.P. 20, would be obtained. It has also been observed, however, that higher D.P. products will be obtained even when using as the sole saccharide source a material such as dextrose which is a monomer. Accordingly, the products obtained result not only from acetal formation but also from polymerization. Similarly, some of the higher D.P. materials may be hydrolyzed in processing to give lower D.P. glycosides. Preferably, the D.P. of the glycosides herein is from 1.0 to 15, preferably 1.5 to 6 when a polyglycoside is the product. The preferred glycoside herein is a glucoside. The term glycoside also embraces derivatives of glycosides such as the alkylene oxide adducts of Mansfield (U.S. Pat. No. 3,640,998 issued Feb. 8, 1972).

The alcohol which is generated by the transalcoholysis route may be removed or left in the reaction mixture during the initial stages. As it is desirable to have only the long-chain alkyl glycoside present for its intended use as a surfactant, the alcohol is desirably removed. This is not only for purposes of enhancing the surfactancy of the composition but the removal of alcohol also minimizes the amount of bleaching agent which is required.

It has been found herein that while a source of sulfur dioxide as later described might be utilized as the bleaching agent, such is not desirable. Basically, the source of sulfur dioxide does not have the requisite strength to sufficiently bleach the dark amber mixture to the desirable straw yellow color. Accordingly, a stronger and more effective bleaching agent must be utilized in the present invention. Bleaching agents which may be employed herein include ozone, hydrogen peroxide, hypochlorite salts, chlorine dioxide, percarbonates, persulfates and peracetates.

The preferred bleaching agent is hydrogen peroxide as it has been determined that the other materials are either too harsh, economically prohibitive, result in salts being present, or are not sufficiently soluble. Hydrogen peroxide by-products are oxygen and water, therefore it is ideally suitable for bleaching. As the products herein are commercially sold as aqueous mixtures, the presence of water is not a significant factor.

The purpose of bleaching the products is to eliminate polyunsaturated conjugated compounds which are formed in making the glycosides. The source of sulfur dioxide stabilizes the bleached product. In the absence of bleaching, the sulfur dioxide will not result in a desirable product color. When both bleaching and sulfur dioxide treatment are practiced, the color is lightened and maintained in a light state. Bleaching alone will lighten the product, however, the product will darken upon aging. Hence, color is not simply improved by the treatment of the present invention but is also stabilized.

The amount of hydrogen peroxide employed in the bleaching of the glycoside is expressed at 1 part of the glycoside to from about 2,000 ppm to about 100,000 ppm of the hydrogen peroxide, preferably from about 5,000 ppm to about 50,000 ppm. Other bleaching agents used herein are similarly converted on an equivalent basis of their ability to generate a free radical.

The bleaching is conducted at from about 15° C. to about 120° C., preferably about 40° C. to about 100° C. As the preferred bleaching agent (hydrogen peroxide) is subject to evaporative losses, the reaction is preferably conducted in a closed vessel at from about 1 to about 20 atmospheres pressure.

The reaction mixture subject to bleaching preferably contains on a dry solids basis from about 15% to about 75% by weight alkyl glycosides, more preferably from about 35% to about 65% by weight. The composition also contains from about 5% to about 85% water, preferably from about 35% to about 65% by weight. The free fatty alcohol content in the mixture to be bleached should be less than about 3%, preferably less than 1.5% by weight. In the mixture to be bleached, the D.P. range of the polyglycoside is generally from about 1.5 to about 15, preferably from about 2 to about 8 on average. Viscosity modifiers such as ethylene glycol, ethanol and the like may also be included.

Following the bleaching of the reaction mixture, the product is exposed to a source of sulfur dioxide. Various sources of sulfur dioxide may be utilized including sulfur dioxide gas, sodium sulfite, sodium bisulfite, sodium metabisulfite, sodium hydrosulfite, potassium sulfite, potassium bisulfite and mixtures thereof. Sulfurous acid may be utilized, however, it is desirable that there then be a source of alkalinity within the reaction mixture so that the sulfur dioxide gas is not lost to the atmosphere.

The amount of sulfur dioxide which is utilized is at 1 part of the organic material to be treated per 50 ppm to about 20,000 ppm of the sulfur dioxide, preferably from about 300 ppm to about 5,000 ppm. A more preferred range for the utilization of the sulfur dioxide is 1 part of the organic material per about 500 ppm to about 2,500 ppm of sulfur dioxide.

As previously noted, it is desirable that the product have a slightly alkaline character as the sulfur dioxide should substantially remain in the mixture with the glycoside during the entire shelf-life of the product. Therefore, the product should be formulated such that the pH is maintained between about 3.5 and about 11, preferably from greater than about 6, to about 9. Similarly, the product should contain preferably at least about 200 ppm of sulfur dioxide per part of organic material within the product, preferably about 350 ppm and most preferably about 500 ppm per part glycoside. As an additional benefit, the source of sulfur dioxide functions as an antimicrobial agent in the product.

The source of sulfur dioxide should not be added to the reaction mixture until the hydrogen peroxide level is below about 5,000 ppm by weight per 1 part of the organic material present. Most preferably, the sulfur dioxide is not added until the hydrogen peroxide is less than about 2,000 ppm.

The reason for not adding the source of sulfur dioxide until the hydrogen peroxide is depleted is that there is a reaction between the hydrogen peroxide and the sulfur dioxide. That is, if the sulfur dioxide is added too soon, then the bleaching effect of the hydrogen peroxide is minimized and the sulfur dioxide needed to stabilize the color properties of the composition is depleted also.

The alkyl glycosides obtained from the present invention are useful for all manner of products in which alkyl glycosides have previously been utilized. Specifically, products of the present invention include cosmetics, light- and heavy-duty dishwashing compositions, built granular detergent products, foaming compositions and industrial chemicals such as oil well drilling fluids.

The following are examples of the present invention.

EXAMPLE I

An alkyl polyglucoside is obtained wherein the alkyl portion is a mixture of $C_{12}$ and $C_{13}$ linear groups. The degree of polymerization (D.P.) of the glucoside is 2.7 and is obtained as 56% solids in an aqueous solution.

The foregoing material which is a dark amber liquid is blended with 2% hydrogen peroxide on a dry solids basis at an adjusted pH of 7.5 to 8. The bleaching is continued at from 65° C. to 68° C. for a period of 20 hours at which time the residual hydrogen peroxide is 0.18% by weight of the organic material present.

The product is tested for its transmittance at a 30% solids content at 470 nanometers.

The results of the transmittance test is as shown in Table I below. The amount of sulfur dioxide added is shown as the weight of sodium bisulfite which is used as the source of $SO_2$. The test in Table I is conducted following aging of the product described above for 20 hours at 95° C. The sodium bisulfite is added immediately prior to the aging test.

TABLE I

| % T* | % Sodium Bisulfite Added |
|---|---|
| 0.05 | 0.0 |
| 39.1 | 0.1 |
| 67.1 | 0.25 |
| 78.2 | 0.50 |
| 80.0 | 1.15 |

*% Transmittance

Table I shows that increased levels of sodium bisulfite result in a lighter colored product.

EXAMPLE II

A glycoside is obtained and bleached as described in Example I. The product is tested for its storage stability at varying levels of sulfur dioxide addition through the use of sodium bisulfite. The storage stability test is run at 50° C. at the pH shown in Table II below. The initial percent transmittance at 30% concentration was 89 at pH 7.0 in the absence of any sodium bisulfite.

TABLE II

| pH | 24 Hrs | 140 Hrs | 260 Hrs | 920 Hrs | % Sodium Bisulfite |
|---|---|---|---|---|---|
| 7.5 | 90.3 | 61.9 | 48.6 | 20.3 | 0 |
| 7.5 | 82.5 | 74.2 | 76.6 | 67.5 | 1.8 |
| 5.5 | 80.4 | 63.8 | 50.4 | 16.5 | 0 |
| 5.5 | 84.8 | 89.4 | 86.7 | 82.2 | 1.8 |

Table II shows that color-stability of the product drops substantially when no source of sulfur dioxide is present in a bleached product. The % transmittance is shown at the times indicated above.

We claim:

1. A process for bleaching glycosides selected from the group consisting of mono and polyglycosides and mixtures thereof comprising the steps of:
    (a) exposing the glycoside material to hydrogen peroxide; and
    (b) exposing the mixture of the glycoside material and the hydrogen peroxide to a source of sulfur dioxide; and recovering the bleached glycoside material from the process.

2. A process for bleaching glycosides selected from the group consisting of mono and polyglycosides and mixtures thereof comprising the steps of:
    (a) exposing the glycoside material to a first bleaching agent; and
    (b) then exposing the mixture of the glycoside material and the first bleaching agent to a source of sulfur dioxide in salt form; and
recovering the bleached glycoside material from the process.

3. A process for stabilizing the color of glycosides comprising the steps of:
    (a) obtaining an aqueous solution of a glycoside;
    (b) thereafter introducing a sufficient amount of a source of sulfur dioxide to stabilize the color of the glycoside,
thereby substantially avoiding color degradation of the glycoside.

4. A composition of matter comprising a bleached glycoside and a sufficient amount of a source of sulfur dioxide to substantially inhibit color degradation of the glycoside.

5. The process or composition of claims 1, 2, 3, or 4 wherein the source of sulfur dioxide is a member selected from the group consisting of sulfur dioxide, sodium bisulfite, sodium metabisulfite, sodium sulfite, sodium hydrosulfite, potassium sulfite, potassium bisulfite and mixtures thereof.

6. The composition of claim 4 wherein there is at least 200 ppm of sulfur dioxide per part glycoside.

7. The process of claim 2 wherein the bleaching agent is hydrogen peroxide and the source of sulfur dioxide is sodium bisulfite.

8. The process of claim 1 wherein the source of sulfur dioxide is not added until the hydrogen peroxide is substantially depleted.

9. The process or composition of claims 1, 2, 3 or 4 wherein the D.P. of the glycoside is from about 1.5 to about 15.

10. The process or composition of claims 1, 2, 4, or 4 wherein the glycoside is a glucoside.

11. The process or composition of claims 1, 2, 3, or 4 wherein the the glycoside is an alkyl glycoside and the alkyl portion contains from 6 to 22 carbon atoms.

12. The process or composition of claim 1 wherein the glycoside is a monoglycoside.

* * * * *